United States Patent
Chen et al.

(10) Patent No.: US 11,701,005 B2
(45) Date of Patent: Jul. 18, 2023

(54) TEMPERATURE MEASUREMENT

(71) Applicant: Nokia Technologies Oy, Espoo (FI)

(72) Inventors: Zhigang Chen, Beijing (CN); Chang Liu, Beijing (CN); Ziming Liu, Beijing (CN); Weidong Meng, Beijing (CN)

(73) Assignee: NOKIA TECHNOLOGIES OY, Espoo (FI)

( * ) Notice: Subject to any disclaimer, the term of this patent is extended or adjusted under 35 U.S.C. 154(b) by 142 days.

(21) Appl. No.: 16/955,686

(22) PCT Filed: Dec. 21, 2017

(86) PCT No.: PCT/CN2017/117740
§ 371 (c)(1),
(2) Date: Jun. 18, 2020

(87) PCT Pub. No.: WO2019/119352
PCT Pub. Date: Jun. 27, 2019

(65) Prior Publication Data
US 2021/0161393 A1   Jun. 3, 2021

(51) Int. Cl.
*A61B 5/01*     (2006.01)
*G16H 40/60*    (2018.01)
(Continued)

(52) U.S. Cl.
CPC .............. *A61B 5/01* (2013.01); *A61B 5/0008* (2013.01); *A61B 5/053* (2013.01); *G16H 40/60* (2018.01);
(Continued)

(58) Field of Classification Search
CPC .......... A61B 5/01; A61B 5/0008; A61B 5/053
See application file for complete search history.

(56) References Cited

U.S. PATENT DOCUMENTS

| 5,632,555 A  | 5/1997 | Gregory et al. |
| 7,249,883 B2 | 7/2007 | Kuroda et al.  |

(Continued)

FOREIGN PATENT DOCUMENTS

| CN | 103932676 A | 7/2014 |
| CN | 104350365 A | 2/2015 |

(Continued)

OTHER PUBLICATIONS

Extended European Search Report received for corresponding European Patent Application No. 17935426.1, dated Jul. 29, 2021, 6 pages.

(Continued)

*Primary Examiner* — Sean P Dougherty
(74) *Attorney, Agent, or Firm* — Alston & Bird LLP (57) ABSTRACT

An apparatus is provided for receiving an indication of a temperature measurement made at a site on a body, the first measurement being of a first type; receiving an indication of an electrical measurement of one or more electrical characteristics made at the site where the temperature measurement was made; determining, based at least in part on the measurement of the one or more electrical characteristics, the site on the body where the temperature measurement was made; associating the measured temperature with the determined site. A method and a computer program product are also provided.

18 Claims, 6 Drawing Sheets

(51) Int. Cl.
*A61B 5/00* (2006.01)
*A61B 5/053* (2021.01)

(52) U.S. Cl.
CPC .............. *A61B 5/741* (2013.01); *A61B 5/742* (2013.01); *A61B 5/749* (2013.01)

(56) References Cited

U.S. PATENT DOCUMENTS

| | | | |
|---|---|---|---|
| 9,404,813 B2* | 8/2016 | Kinsley | G01J 5/021 |
| 9,645,013 B2 | 5/2017 | Thrush | |
| 2011/0228810 A1 | 9/2011 | O'Hara et al. | |
| 2012/0198715 A1 | 8/2012 | Eaton | |
| 2013/0085707 A1* | 4/2013 | Holderle | G01J 5/026 |
| | | | 702/130 |
| 2013/0245489 A1* | 9/2013 | Mullin | A61B 5/0084 |
| | | | 600/549 |
| 2014/0046192 A1 | 2/2014 | Mullin et al. | |
| 2014/0064331 A1* | 3/2014 | Mullin | G01J 5/025 |
| | | | 374/158 |
| 2014/0064333 A1 | 3/2014 | Roth | |
| 2014/0330266 A1* | 11/2014 | Thompson | A61B 18/1206 |
| | | | 606/34 |
| 2015/0139277 A1 | 5/2015 | Segal et al. | |
| 2015/0185086 A1 | 7/2015 | Al-Faifi | |
| 2015/0198489 A1* | 7/2015 | Kinsley | G01J 5/0025 |
| | | | 29/595 |
| 2016/0081559 A1 | 3/2016 | Sofia et al. | |
| 2016/0150975 A1* | 6/2016 | Mullin | A61B 5/01 |
| | | | 600/549 |
| 2017/0258334 A1* | 9/2017 | Miller | A61B 5/01 |
| 2018/0055371 A1* | 3/2018 | Mullin | A61B 5/01 |

FOREIGN PATENT DOCUMENTS

| | | | | |
|---|---|---|---|---|
| CN | 105078420 A | | 11/2015 | |
| CN | 105209871 A | | 12/2015 | |
| CN | 106031630 A | | 10/2016 | |
| CN | 106716090 A | | 5/2017 | |
| CN | 107405112 A | * | 11/2017 | ........... A61B 5/0022 |
| DE | 102013000966 A1 | * | 7/2014 | ............... A61B 5/01 |
| EP | 2428782 A2 | * | 3/2012 | ............... A61B 5/01 |
| EP | 2519143 A4 | * | 1/2016 | ............... G01K 1/02 |
| WO | WO-2006078459 A2 | * | 7/2006 | ............. A61B 18/10 |
| WO | WO-2014114433 A1 | * | 7/2014 | ............... A61B 5/01 |
| WO | 2017/079849 A1 | | 5/2017 | |

OTHER PUBLICATIONS

"Best Armpit Thermometer Reviews 2016", Apollo Build Tec, Retrieved on Jul. 31, 2017, Webpage available at: http://www.apollobuildtec.com/best-armpit-thermometer-reviews-2016/.
International Search Report and Written Opinion received for corresponding Patent Cooperation Treaty Application No. PCT/CN2017/117740, dated Sep. 28, 2018, 10 pages.
Office Action for Chinese Application No. 201780098221.9 dated Feb. 28, 2023, 13 pages.

* cited by examiner

TEMPERATURE MEASUREMENT

RELATED APPLICATION

This application claims priority to PCT Application No. PCT/CN2017/117740, filed on Dec. 21, 2017, which is incorporated herein by reference in its entirety.

TECHNICAL FIELD

The present application relates generally to an apparatus such as a thermometer for determining the temperature at various locations on a human or animal body.

BACKGROUND

Thermometers can be used to determine an approximation of the core temperature of a human or animal body. One type of thermometer determines the electrical characteristics of a thermistor placed at a site on the body to determine the temperature at that site. If a suitable site is chosen, the determined temperature will be close to the core temperature of the body. The determined temperature is an approximation of the core temperature because the ambient temperature of the environment in which the body is located will normally have a heating or cooling effect on the periphery of the body, where convenient sites for temperature measurement are normally located. Such sites include the axilla (e.g. the armpit of a human body), the oral cavity (i.e. inside the mouth), and the rectum (the thermometer being inserted through the anus).

So-called "smart thermometers" may have functions that compliment temperature measurement. For example, some smart thermometers are able to store historical temperature readings, and some allow readings to be communicated to other devices, for example to a mobile telephone, where the readings may be stored, analysed, or otherwise processed.

SUMMARY OF THE INVENTION

In a first example aspect, there is provided an apparatus comprising at least one processor and at least one memory including computer program code, the at least one memory and the computer program code configured to, with the at least one processor, cause the apparatus at least to: receive an indication of a temperature measurement made at a site on a body, the first measurement being of a first type; receive an indication of an electrical measurement of one or more electrical characteristics made at the site where the temperature measurement was made; determine, based at least in part on the measurement of the one or more electrical characteristics, the site on the body where the temperature measurement was made; associate the measured temperature with the determined site.

In a second example aspect, there is provided a method comprising: receiving an indication of a temperature measurement made at a site on a body, the first measurement being of a first type; receiving an indication of an electrical measurement of one or more electrical characteristics made at the site where the temperature measurement was made; determining, based at least in part on the measurement of the one or more electrical characteristics, the site on the body where the temperature measurement was made; associating the measured temperature with the determined site.

In a third example aspect, there is provided a computer program product comprising a computer-readable medium bearing computer program code embodied therein for use with a computer, the computer program code comprising: instructions for receiving an indication of a temperature measurement made at a site on a body, the first measurement being of a first type; instructions for receiving an indication of an electrical measurement of one or more electrical characteristics made at the site where the temperature measurement was made; instructions for determining, based at least in part on the measurement of the one or more electrical characteristics, the site on the body where the temperature measurement was made; instructions for associating the measured temperature with the determined site.

In a fourth example aspect, there is provided an apparatus comprising means for: receiving an indication of a temperature measurement made at a site on a body, the first measurement being of a first type; receiving an indication of an electrical measurement of one or more electrical characteristics made at the site where the temperature measurement was made; determining, based at least in part on the measurement of the one or more electrical characteristics, the site on the body where the temperature measurement was made; associating the measured temperature with the determined site.

BRIEF DESCRIPTION OF THE DRAWINGS

For a more complete understanding of example embodiments of the present invention, reference is now made to the following descriptions taken in connection with the accompanying drawings in which:

FIGS. 4a-8a are drawings of the exterior of the sensor tips of FIGS. 4-8;

DETAILED DESCRIPTION OF THE DRAWINGS

Figure 1:
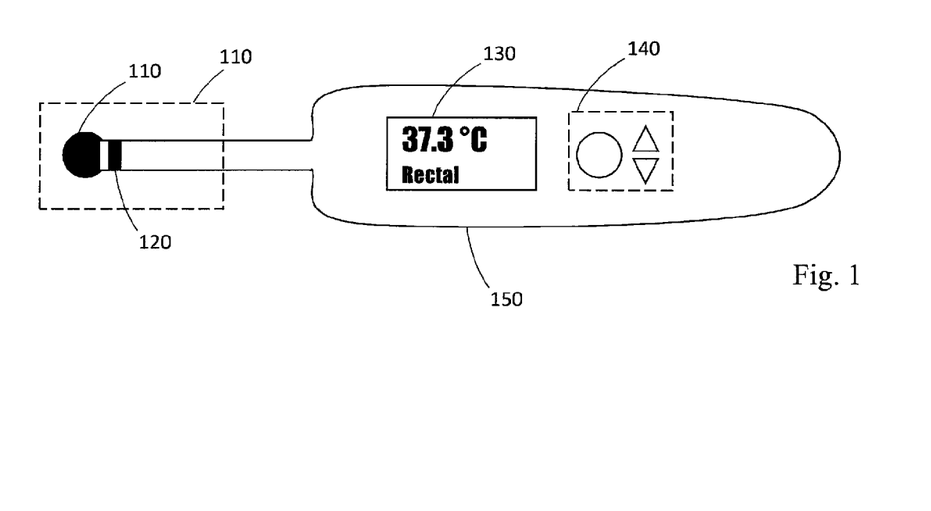
FIG. 1 shows an example of an apparatus.

FIG. 1 shows an example of an apparatus which is, in this case, a thermometer 100. The thermometer has a sensor tip part 101, various examples of which are shown in greater detail in FIGS. 4-8 and 4a-8a. The sensor tip 100 includes a temperature sensor mounted inside a protective enclosure 110, and two or more electrodes 120. It is not strictly necessary to enclose the temperature sensor, but doing so may have the advantage that the sensor is protected from contamination from the user's body by the enclosure 110, which may be easier to clean. Additionally, the sensor may have conductive parts (e.g. electrical contacts) that may be short-circuited by the user's body with the effect that temperature readings become inaccurate, so the protective enclosure 110 may shield the temperature probe from direct contact with the user's body to prevent this.

Any suitable technology may be used for the temperature sensors. For example, the temperature sensor may be a thermistor, a thermocouple, a resistance thermometer, or a silicon bandgap temperature sensor. Commonly a thermistor is used in consumer thermometers because it is simple, accurate, and cheap.

The thermometer is also provided with a display 130 and a user interface 140. In this example a display is used to communicate a temperature reading to the user, although of course any alternative approach may be used. For example, an audio transducer may be provided in place or in addition to the display 130, with the reading being communicated via an audio output such as a speech output. Any other suitable form of output device may be used. The thermometer 100 may, of course, not comprise its own output device for communicating a reading directly to the user—instead it may use an interface such as a wired or wireless interface to communicate the reading to another device to which the user has access. For example, the thermometer 100 may communicate a reading to a user device such as a smartphone, tablet, personal computer, or smartwatch, with the user being able to access the reading on that device. The thermometer 100 may even upload the reading to the cloud, with the user then connecting to a remote service to access it from a user device. In some examples, the user may not have any access at all to the temperature—it may, for example, be communicated to a service that monitors the temperature but does not make available to the user the reading itself.

Any suitable user interface 140 may be provided. In the example shown in FIG. 1, three buttons are provided for the user to navigate and initiate functions of the thermometer 100. For example, the user may press one of the buttons 140 to initiate a temperature reading. Other possible user interface might include motion sensors (e.g. the user taps the thermometer to initiate a reading), touch sensors, a microphone for receiving voice commands, etc. In some examples there may be no user interface 140 at all, with temperature readings being taken automatically—for example continuously, periodically, or in response to detected event such as a movement of the thermometer, detected presence of a body, etc.

The thermometer 100 is enclosed in a housing 150 to protect it, e.g. from physical damage or from contamination. The housing may be elongate, with the temperature sensor at a proximate end and a grip at a distil end, so that the user can securely hold the thermometer 100 and easily position or insert the temperature sensor at a site on the body.

Figure 2:
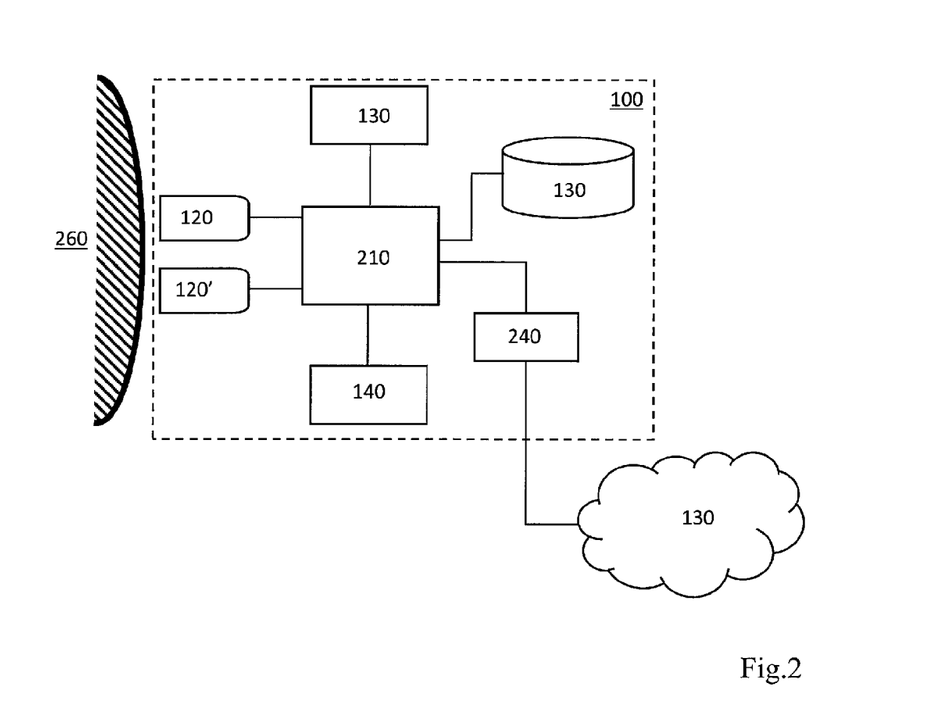
FIG. 2 is a schematic drawing of the apparatus of FIG. 1.

FIG. 2 shows a schematic drawing of the thermometer 100 of the example of FIG. 1. Shown is a processor 210 that controls the operation of the thermometer based on program instructions that are stored in a memory 220 accessible by the processor. Together the processor and memory may be referred to as control circuitry. Other forms of control circuitry may be used in place of a processor and memory, for example a dedicated circuit of discrete components, an integrated circuit such as application specific integrated circuit, a field programmable gate array, or any other suitable circuit for controlling the operation of the thermometer 100.

Also shown in FIG. 2 are the display 130 and user interface 140 described above, together with an interface 240 for communicating with one or more external devices 240, for example over a wired or wireless connection. The interface may be a short range radio interface such as Bluetooth or Bluetooth LE.

Also shown in FIG. 2 are the temperature sensor 230 and two electrodes 120 and 120'. These electrodes 120, 120' are positioned to contact a body 260 when the temperature sensor 230 is used to record its temperature. In practice more than two electrodes may be used, and the use of more than two electrodes may ensure that at least a pair of electrodes contact the user's body 250 when the positioning of the thermometer 100 relative to the body 250 means that not every electrode will contact the body 250. When two or more electrodes 120, 120' contact the body, the electrical properties of the body between the electrodes may be determined by analysing signals across the electrodes.

In some embodiments the connection between the control circuitry and each of the temperature sensor 230 and the electrodes 120, 120' is separate, with (for example) separate wired connections to each of the temperature sensor 230 and each electrode 120, 120'. Typically a temperature sensor (e.g. a thermistor) may require just two connecting wires, so four wires may be present in total.

However, in other embodiments the connection between the control circuitry and the temperature sensor 230 may be combined with the connection to one of the electrodes 120, 120'. An example of such an arrangement is shown in the circuit diagram of FIG. 3.

Figure 3:
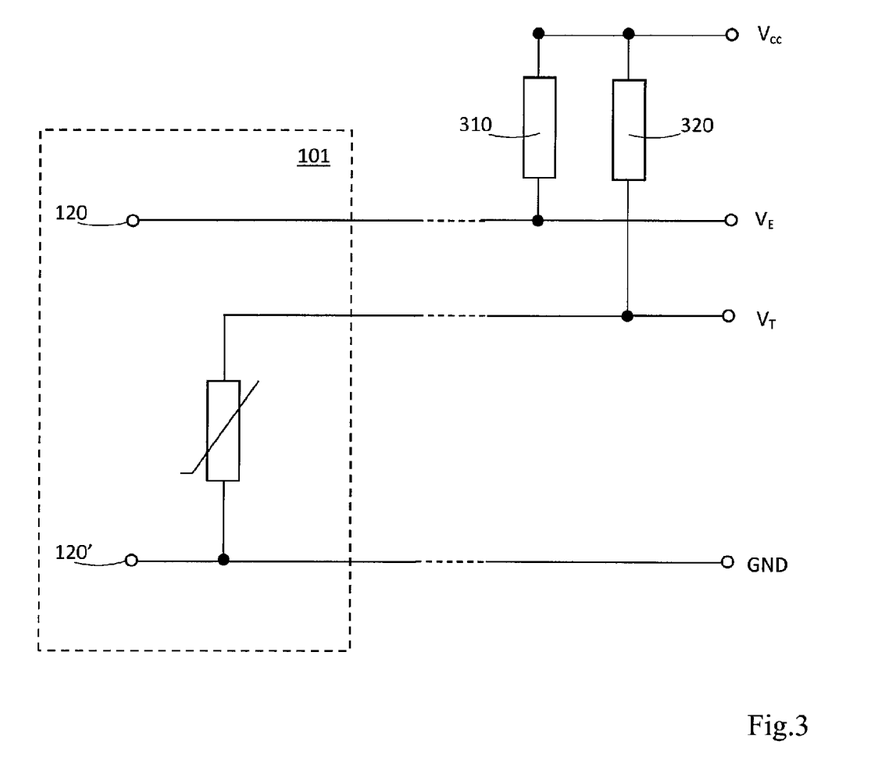
FIG. 3 is a circuit diagram of an example sensor tip.

FIG. 3 shows a circuit comprising two voltage dividers. The first is represented by the series connection of resistor 320 and thermistor 330, which in this example is the temperature sensor 230. A potential difference $V_{cc}$ is applied across these series-connected resistors and an output $V_T$ connected between them. The voltage recorded at the output $V_T$ varies in proportion to the temperature of the thermistor, according to the known properties of the thermistor used, and can therefore be used to determine the temperature at the thermistor.

A second voltage divider is formed by resistor 310 which is connected in series to the electrodes 120 and 120' with $V_{cc}$ applied across the divider. When the electrodes contact a body the resistance (e.g. skin resistance) of the body forms the second resistance in the voltage divider and measurement of the voltage at output $V_E$, located between resistor 310 and the electrodes 120, 120' allows the resistance between the electrodes to be determined.

FIG. 3 highlights those components that would be contained within the sensor tip 101. Note that in this example only three electrical connections (e.g. circuit board tracks or wires) are needed to the sensor tip 101 since the thermistor and electrode potential dividers share a common ground wire GND. They could alternatively share a common voltage supply connection directly from Vcc, with resistors 310 and 320 being positioned between outputs $V_E$ and $V_T$ and ground GND. Alternatively, the electrodes and thermistor could be provided with completely separate connections, in this example requiring four separate connectors to the sensor tip 101. Other electrical arrangements would be possible for the skilled person having the knowledge contained within the present disclosure.

Reducing the number of connections required to the sensor tip 101 simplifies the construction of the thermometer, reduces the size of the housing required between the sensor tip 101 and the rest of the thermometer, and reduces manufacturing costs.

Various possible configurations of sensor tip (for example the sensor tip 101 of FIG. 1) are shown in FIGS. 4-8 and corresponding FIGS. 4a to 8a. These are presented only examples, and not as an exhaustive list of possible configurations.

Figure 4:
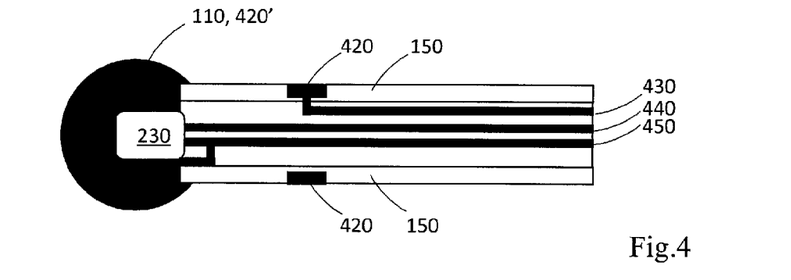
FIGS. 4-8 are cross section drawings of example sensor tips.
Figure 4A:
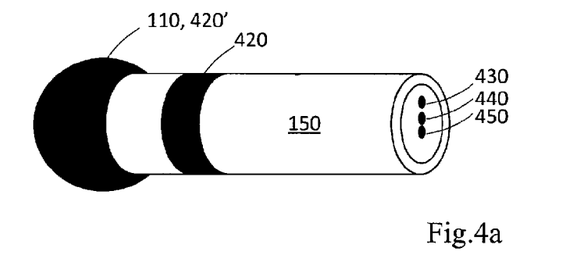

FIG. 4a shows a sensor tip which benefits from the three-connector arrangement described above. In this example the protective enclosure 110 is not only thermally conductive, to permit the temperature sensor 230 to rapidly reach the temperature of the body when the thermometer is un use, but is also electrically conductive in order that it can be used as one of the electrodes, in this case electrode 420'. The second electrode 420 is spaced apart from the first 420' be an insulating material, in this case the housing 150 of the thermometer. Several conductors run through the housing 150, which may be hollow, solid, or filled with a suitable material (e.g. an insulating material). Conductor 430 connects to electrode 420, connector 440 connects to the temperature sensor 230, and connector 450 connects to both the temperature sensor and the electrically conductive protective enclosure 110 protecting the temperature sensor 230. The other ends of the conductors couple these various components to the control circuitry of the thermometer.

In the example of FIG. 4, electrode 420 comprises a conductive ring on the exterior of the housing 150. This ring can be better appreciated from FIG. 4a, which is an exterior drawing of the sensor tip shown in FIG. 4. It is not necessarily the case that electrode 420 is in the shape of a complete ring. For example, the electrode may be shaped as a broken ring, a circle, a square, or indeed any other shape. However, a ring (or at least a shape that extends fully around the housing, has the advantage that the electrode is not dependent upon a particular orientation of the thermometer in order to make contact with the body.

Figure 5:
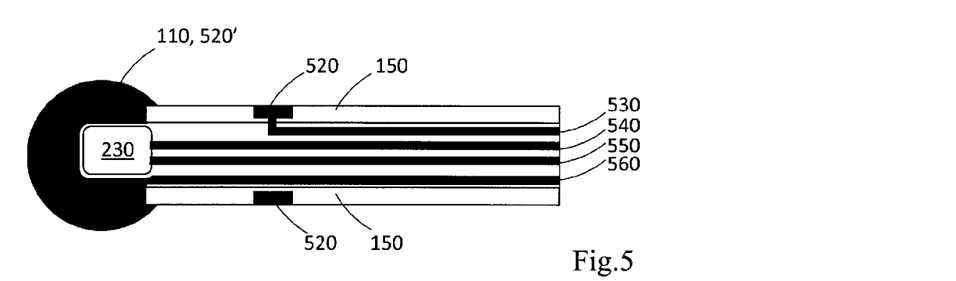

FIG. 5 shows an example that is similar to the sensor tip shown in FIG. 4, but uses a four-conductor arrangement in place of FIG. 4's three-conductor arrangement. Here conductor 530 connects to electrode 520 (again illustrated, by way of example only, as a continuous ring around the exterior of the housing 150), conductors 540 and 550 connect to the temperature sensor 230, and conductor 560 connects to the second electrode (again illustrated, by way of example only, as the protective enclosure 110 around the temperature sensor 230).

Figure 5A:
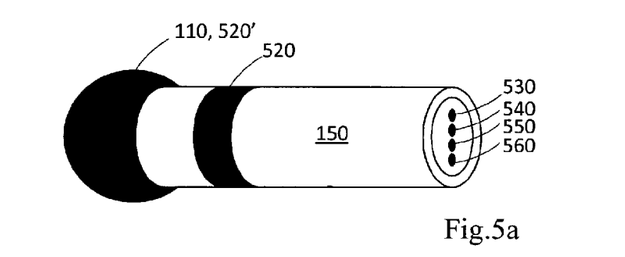

FIG. 5a is an exterior drawing of the sensor tip shown in FIG. 5. It is similar in appearance to that of FIG. 4a, aside from the presence of the additional conductor 560.

Figure 6:
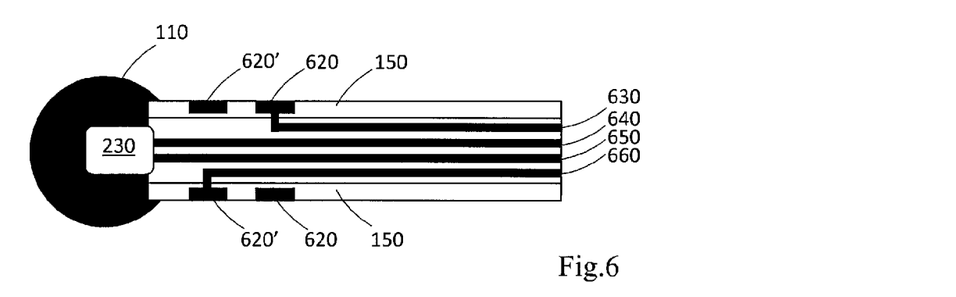

FIG. 6 illustrates an example of a sensor tip where the protective enclosure 110 does not form one of the electrodes, and need not therefore be electrically conductive. Instead, the electrodes 620, 620' are both provided as conductive rings around the housing 150, each connected to a different conductor 630, 660. The temperature sensor 230 is in this example connected to the control circuitry via its own separate conductors 640, 650; however, it could alternatively share a conductor with one of the electrodes as previously described.

Figure 6A:
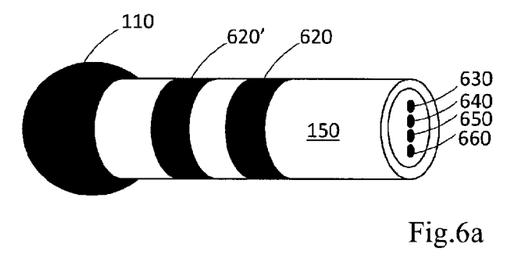

FIG. 6a is an external view of the sensor tip shown in FIG. 6. Whilst the two electrodes 620, 620' are shown here as parallel rings, it should be understood that they could have any shape so long as they are not in direct electrical connection with one another and are positioned so that at least a portion of each electrode 620, 620' will contact the body when the thermometer is in use.

Figure 7:
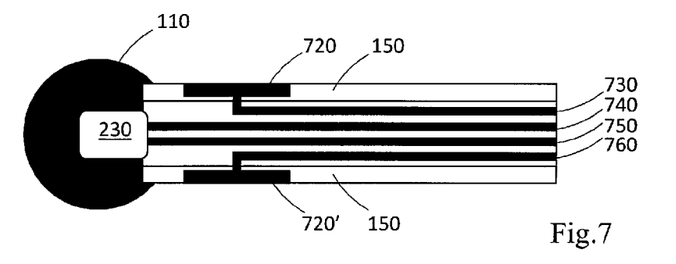
Figure 7A:
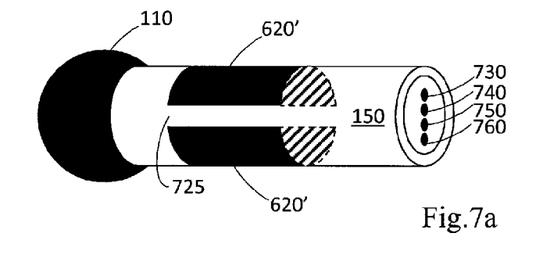

FIGS. 7 and 7a shows an alternative shape of the electrodes used in FIGS. 6 and 6a. Rather than being configured as parallel rings, the electrodes 720, 720' are instead formed as rectangles wrapped around opposite sides of the housing 150. As explained above, any shape of electrode could have been used in place of the rectangles, but the rectangles may provide for increased ease of manufacture since they may be formed of a single ring with two straight cuts 725 then made to separate them. The conductors 730, 340, 750, 760 couple the electrodes 720, 720' and the temperature sensor 230 to the control circuitry.

Figure 8:
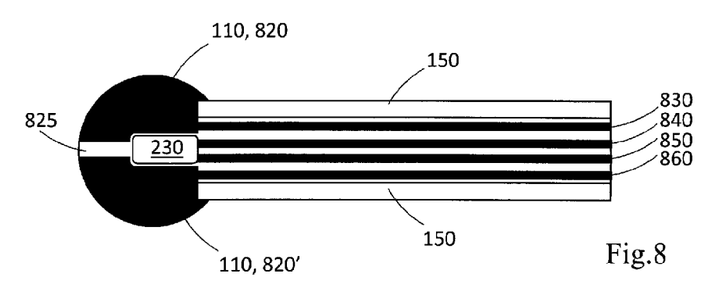
Figure 8A:
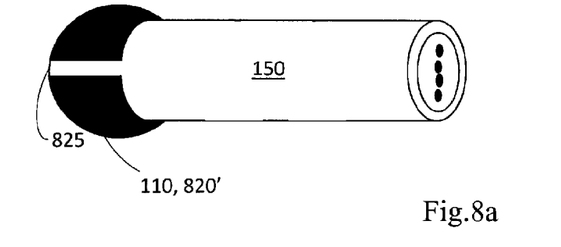

FIGS. 8 and 8a again show an alternative arrangement of the electrodes. Here both electrodes 820, 820' are formed as part of the protective enclosure 110 around the temperature sensor 230. In the example shown these figures each electrode 820, 820' is shaped as an approximate hemisphere, but any shape of electrode could be used so long as the electrodes 820, 820' are electrically separated from one another. In FIGS. 8 and 8a, this electrical separation is achieved by forming a gap between the electrodes 825, which may be (for example) in-filled with an insulating material.

Forming the electrodes 820, 820' on the protective enclosure 110 may provide the advantage that they will both contact the body when a temperature reading is being taken without requiring the user to take special care as to the position and orientation of the thermometer, because it is normal for a thermometer to be positioned such that the protective enclosure and therefore the temperature sensor is substantially enclosed by a body whilst a temperature reading of that body is taken.

As has been previously described, the electrodes 120, 120' are designed and positioned such that when the thermometer 100 is used to take a temperature reading of a site on a body then the electrodes will contact the body at that site. Such contact may be contact with solid body parts such as skin, or with body liquids such as saliva or mucus. The electrodes may be used to measure the electrical properties of the body at the site. For example, the use of a voltage divider has been previously described for measuring a resistance of the body at the site, but any other suitable approach may be used—for example a Wheatstone bridge. Other electrical characteristics may also be measured, for example the capacitance of the body. A combination of characteristics may be measured, for example both the resistance and capacitance of the body.

The electrical characteristics of a human or animal body vary from site to site. One reason for this variance the wetness or dryness of the body at different sites. For example, the oral cavity would normally have a much lower resistance than the axilla for the reason that the axilla is normally relatively dry with conductance provided by the skin of the body, whereas the oral cavity is normally wet with oral fluid, providing a better electrical connection to electrodes inserted therein and also higher conductivity through the fluids than would be present for the dry skin of the axilla. Similarly, the capacitance of a body will vary from site to site, for example dependent upon the thickness and dryness of the skin at each site (thicker and drier layers of skin providing a more substantial insulating layer between an electrode and the largely conductive moist body tissue underneath the skin).

Consequently, knowledge of the electrical characteristics of the skin at a particular site allow the location of the site on the body to be estimated. When the site is known to be one of a number of sites with drastically different electrical properties then such estimation can be performed with a very high level of certainty.

In the following example, reference will be made to resistance, but it is to be understood that other electrical characteristics may be equally applicable.

Three body sites that are commonly used for temperature readings are the oral cavity, axilla, and rectum. Each of the three has a distinct typical range of electrical resistance, the following being examples for a human body:

| Site | Typical Resistance (kΩ) |
| --- | --- |
| Oral cavity | 100-300 |
| Rectum | 700-2,000 |
| Axilla | 5,000-20,000 |

Since the ranges are non-overlapping, measured resistances falling within these ranges can be unambiguously mapped to one of the sites. For example, a resistance of 1 MΩ lies uniquely within the range of rectal resistances and if a thermometer used to take oral, rectal, and axillary measurements takes a temperature measurement when a resistance of 1 MΩ is measured across the electrodes then that temperature can be determined with a strong level of confidence to be a rectal temperature measurement.

When the electrical characteristics do not lie within one of the ranges, or where two ranges overlap, it may not be possible to make an unambiguous determination as to which site a measurement corresponds to. In such cases, a best-guess may be made, with a lower level of confidence in the result. For example, a resistance of 450 kΩ lies outside all three of the above ranges; however, it lies closer to the range for oral resistances than it does to any other range. It may therefore be determined that a temperature reading made with a 450 kΩ resistance between the electrodes corresponds to an oral temperature.

Alternatively, readings that fall outside the range associated with any site may be disregarded, or flagged e.g. as potentially erroneous readings. The unexpected resistance may, for example, be indicative of an erroneous temperature reading—for example a reading that was made when the thermometer was not making proper contact with the intended site.

The ranges themselves may be determined in any suitable manner. For example, the manufacturer of the thermometer, or any other information provider such as a doctor's surgery or hospital, may provide ranges that are stored within the thermometer or accessible by it. The ranges may be generalised across a population, or may be specific to a particular user or group of users, for example based on historical values that may or may not be manually associated with particular sites by the user.

For example, a thermometer may be provided with an initial default set of ranges which are gradually adapted based on uses of the thermometer. By way of further example, a default oral range of 100-300 kΩ may be adapted after a number of readings are received that lie within a range of 70 kΩ-200 kΩ, with the adapted range including that range of received values, or at least being derived at least in part based upon it. The user may manually flag those readings as oral temperatures, or this may be done so automatically based on the 'best guess' of the thermometer and perhaps in part based on a recognition that readings within the default range for oral temperatures typically lie towards the lower end of that range.

For various reasons, different temperature measurement sites on a body will differ in temperature from the core body temperature by varying amounts. Such reasons include variations in the blood supply to different sites, thickness of the skin, and differences in exposure to ambient temperature. For example, it is not common practice to take temperature measurements at the nose—the nose is peripheral to the body and comprises a thin layer of tissue that is exposed to the ambient temperature both inside and out. A temperature measurement made at the nose on a cold day would therefore differ enormously from a similar measurement made on a hot day because of the nose's susceptibility to ambient temperatures. The oral cavity, axilla, and rectum are all preferred sites for temperature measurement because each has a good blood supply and is comparatively enclosed, reducing its susceptibility to the effects of ambient temperatures. However, the rectal temperature is generally closest to the body's core temperature, followed by the oral cavity, followed by the axilla. This relationship may vary, however—for example the oral temperature will be significantly affected by the consumption of hot or cold food or drink immediately prior to a temperature measurement.

It is therefore desirable that a temperature measurement should be associated with the site where it was taken. Doing so provides many advantages, including permitting inferences as to the reliability of the reading (e.g. rectal readings are typically closer to the core temperature and exhibit less variance than oral readings). It may also allow for the correction of readings based on the site, for example by applying a predetermined corrective function specific to the site that corrects temperature readings for that site to an approximation of core temperature.

The determination of a site may also be used as an approach to assign a temperature reading to a particular body. For example, a parent may use the same thermometer to record their own axillary temperature and their child's rectal temperature. Differentiating a set of temperature readings between axilla and rectal readings would permit the parent to observe the separate trends in their own temperature and that of their child without the need to manually associate each reading with the identity of the body it is taken from.

The determination of the site may have advantages in terms of hygiene and user preference for thermometer usage. For example, a user may be unwilling to use a thermometer to take his own oral temperature if he knows that it has been previously used (perhaps by a different user) to take a rectal temperature reading. A thermometer that can sense the site where a temperature reading is taken can alert future users to the previous use of the thermometer at that site—for example by providing a visual and/or audible warning to the user when, for example, the thermometer is switched on. Such a warning may identify the site(s) where the thermometer has previously been used.

Figure 9:
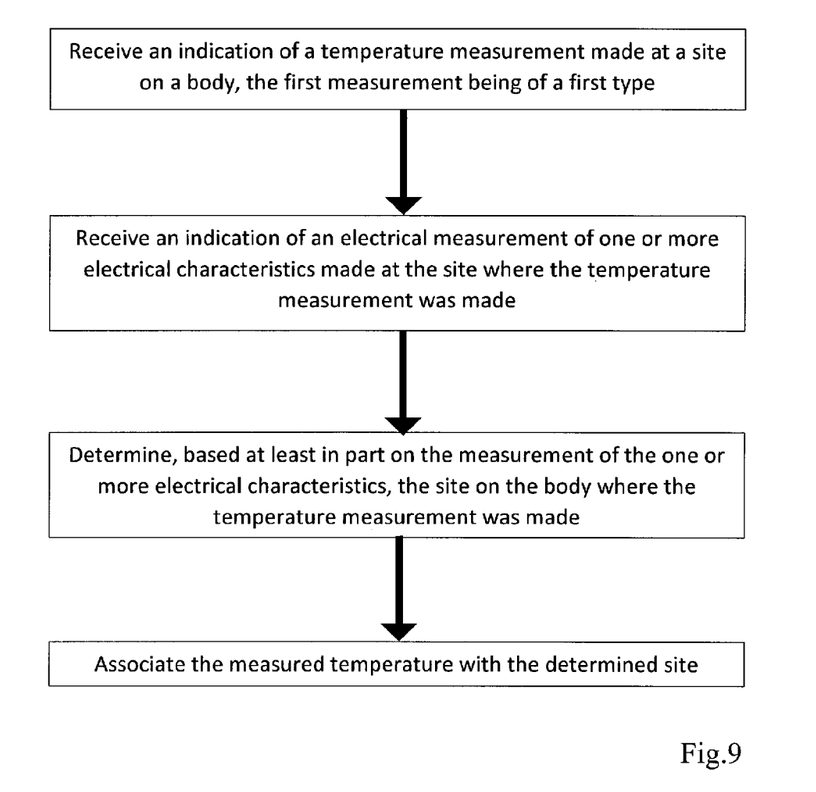
FIG. 9 is a flow chart of an example method.

FIG. 9 illustrates an example method. The method begins at step 900, where an indication of a temperature measurement is received, for example by the control circuitry. In some examples the indication will provide a processed value for the reading, and in others it will provide part-processed or raw sensor date. For example, in the case of a thermometer using a simple thermistor the indication may be a voltage level that requires processing in order to determine a temperature measurement associated with that voltage level.

In step 910, an indication of a measurement of one or more electrical characteristic is received. Again, this indication may be processed, or it may be raw sensor data, for example a potential difference across two electrodes.

The two measurements are made at the same site on the body. The exact location of the two measurements may not be precisely the same e.g. by virtue of the sensors used for each having slightly different physical positions on e.g. a thermometer apparatus, but they will be close enough that the measured electrical characteristic(s) are that of the site of the body where the temperature measurement is taken. For example, where the temperature measurement is oral, the measured electrical characteristics may not be for the precise millimetre location where the temperature reading was taken, but they will be for the oral cavity, enabling a determination that the temperature measurement is an oral one. In practice, the two measurements may be taken within 10 mm of one another, although a greater separation is possible. The location of the two measurements may therefore be considered to be substantially the same.

The two measurements are not necessarily taken in the order shown in FIG. 9. Instead, the measurement of the electrical characteristic(s) may be taken before the temperature measurement. However, in order to limit the possibility of the thermometer being moved between sites between the two measurements, in many examples the two measurements will be performed substantially simultaneously, for example within 500 ms of one another.

In step 920 a determination is then made, based at least in part on the measurement of the one or more electrical characteristics, of the site on the body where the temperature measurement was made. This may be done, for example, by reference to ranges of electrical characteristics that are associated with particular sites, as described previously.

Finally, in step 930, the measured temperature is associated with the site where the temperature measurement is determined to have been made. For example, the measured temperature may be tagged with the determined site before being stored in memory or communicated remotely. The tagging may involve storing the measured temperature and the determined site together as a single record, or for example storing the two separately but in such a way that they can be later associated together.

Figure 10:
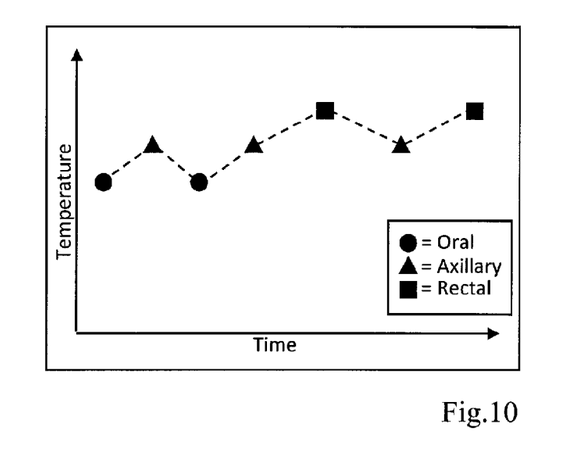
FIGS. 10 and 10a are example visualisations.
Figure 10A:
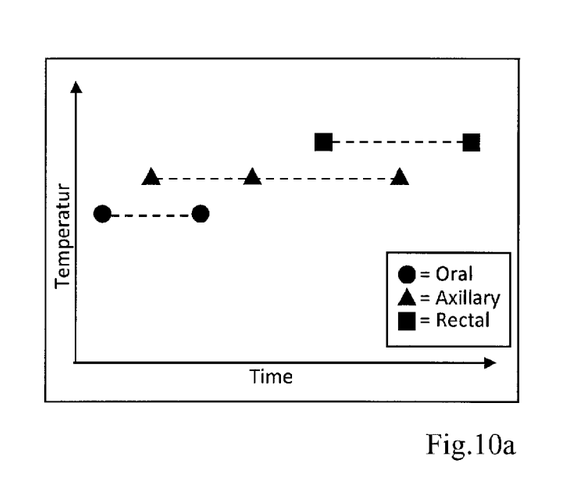

FIGS. 10 and 10a show an example of a visualisation created for the review of a user based on measured temperatures that have been tagged with site. In the visualisation, temperature measurements have been plotted on a vertical temperature axis and a horizontal time axis. Such a visualisation might be provided on a thermometer device, or remotely on the user's smartphone or other device.

FIG. 10 shows a number of temperature measurements showing a general (albeit non-monotonic) increase in temperature that might lead the user to think that the temperature of the body is rising, perhaps indicating an illness.

However, each measurement has been visually differentiated according to the site on the body where it was made, providing additional context to the user. FIG. 10a shows the same measurements plotted on the same axes, but separated according to site. As the user can see, although there are variations in the values of the measurements, they are constant for each site. The user may therefore conclude that whilst he may have obtained different readings over time as he has measured at different sites, there has been no change in his core temperature. The user may therefore conclude that his results are not indicative of an illness.

Although various aspects of the invention are set out in the independent claims, other aspects of the invention comprise other combinations of features from the described example embodiments and/or the dependent claims with the features of the independent claims, and not solely the combinations explicitly set out in the claims.

It is also noted herein that while the above describes example embodiments of the invention, these descriptions should not be viewed in a limiting sense. Rather, there are several variations and modifications which may be made without departing from the scope of the present invention as defined in the appended claims. Furthermore, although particular combinations of features have been described in the context of specific examples, it should be understood that any of the described features may be present in any combination that falls within the scope of the claims.

What is claimed is:

1. An apparatus comprising at least two electrodes, at least one processor and at least one memory including computer program code, the at least one memory and the computer program code configured to, with the at least one processor, cause the apparatus at least to perform:
   receiving an indication of a temperature measurement made at a site on a body;
   receiving an indication of a resistance measurement sensed by at least one of the at least two electrodes at the site where the temperature measurement was made;
   determining, based at least in part on the resistance measurement, the site on the body where the temperature measurement was made;
   associating the measured temperature with the determined site; and
   causing display via a user interface of the temperature measurement and an indication of the associated site where the temperature measurement was made.

2. The apparatus of claim 1, wherein the at least one memory and the computer program code are configured to, with the at least one processor, further cause the apparatus at least to perform:
   storing the measured temperature with the determined site in a memory.

3. The apparatus of claim 1, wherein the at least one memory and the computer program code are configured to, with the at least one processor, further cause the apparatus at least to perform:
   transmitting the measured temperature and the determined site to a remote device.

4. The apparatus of claim 1, wherein determining the site on the body where the temperature measurement was made comprises comparing the indicated resistance measurement to one or more ranges of values associated with known body sites.

5. The apparatus of claim 4, wherein the ranges are based on historical measurements for the body being measured.

6. The apparatus of claim 4, wherein the range associated with the determined site is modified based on the temperature measurement.

7. The apparatus of claim 1, further comprising a housing, wherein at least one of the two or more electrodes comprises is connected to a ring surrounding the housing.

8. The apparatus of any of claim 1, further comprising a plurality of conductors coupling control circuitry to each of the electrodes and to a temperature sensor used to perform the temperature measurement, wherein a first of the conductors couples both the temperature sensors and at least one electrode to the control circuitry.

9. The apparatus according to claim 1, wherein the apparatus comprises a non-electrically conductive enclosure protecting a temperature sensor.

10. A method comprising:
    receiving an indication of a temperature measurement made at a site on a body by a device;
    receiving an indication of a resistance measurement sensed by at least one of at least two electrodes of the device at the site where the temperature measurement was made;
    determining, based at least in part on the resistance measurement, the site on the body where the temperature measurement was made;
    associating the measured temperature with the determined site; and
    causing display via a user interface of the temperature measurement and an indication of the associated site where the temperature measurement was made.

11. The method of claim 10, further comprising:
    storing the measured temperature with the determined site in a memory.

12. The method of claim 10, further comprising:
    transmitting the measured temperature and the determined site to a remote device.

13. The method of claim 10, wherein determining the site on the body where the temperature measurement was made comprises comparing the indicated electrical resistance measurement to one or more ranges of values associated with known body sites.

14. The method of claim 13, wherein the ranges are based on historical measurements for the body being measured.

15. The method of claim 13, wherein the range associated with the determined site is modified based on the temperature measurement.

16. The method according to claim 10, wherein the device comprises a non-electrically conductive enclosure protecting a temperature sensor.

17. A non-transitory computer readable medium comprising program instructions stored thereon for performing at least the following:
- receiving an indication of a temperature measurement made at a site on a body by a device;
- receiving an indication of a resistance measurement sensed by at least one of at least two electrodes of the device at the site where the temperature measurement was made;
- determining, based at least in part on the resistance measurement, the site on the body where the temperature measurement was made;
- associating the measured temperature with the determined site; and
- causing display via a user interface of the temperature measurement and an indication of the associated site where the temperature measurement was made.

18. The non-transitory computer readable medium according to claim 17, wherein the device comprises a non-electrically conductive enclosure protecting a temperature sensor.

* * * * *

UNITED STATES PATENT AND TRADEMARK OFFICE
CERTIFICATE OF CORRECTION

PATENT NO. : 11,701,005 B2
APPLICATION NO. : 16/955686
DATED : July 18, 2023
INVENTOR(S) : Zhigang Chen et al.

Page 1 of 1

It is certified that error appears in the above-identified patent and that said Letters Patent is hereby corrected as shown below:

In the Drawings

In sheet 6 of 6, FIG. 10a, delete "Temperatur" and insert -- Temperature --, therefor.

In the Claims

In Column 10, Line 28, Claim 7, delete "electrodes comprises" and insert -- electrodes --, therefor.

In Column 10, Line 30, Claim 8, delete "of any of claim" and insert -- of claim --, therefor.

Signed and Sealed this
Twentieth Day of February, 2024

Katherine Kelly Vidal
*Director of the United States Patent and Trademark Office*